United States Patent [19]

Reddy et al.

[11] Patent Number: 5,157,051
[45] Date of Patent: Oct. 20, 1992

[54] COMPOSITION AND USE OF 3-THIOCYANO-2-HALO-2-PROPENENITRILES AS ANTIMICROBIAL AGENTS

[75] Inventors: Kalakota S. Reddy; Thomas L. Siddall; Connie L. Deford, all of Midland, Mich.

[73] Assignee: The Dow Chemical Company, Midland, Mich.

[21] Appl. No.: 846,092

[22] Filed: Mar. 5, 1992

[51] Int. Cl.$^5$ .................... A61K 31/26; C07C 331/02
[52] U.S. Cl. ...................................... 514/516; 558/14
[58] Field of Search .......................... 558/14; 514/516

[56] References Cited

U.S. PATENT DOCUMENTS

| | | | |
|---|---|---|---|
| 3,140,306 | 7/1964 | Heininger | 260/465 |
| 4,172,892 | 10/1979 | Nannini et al. | 544/26 |
| 4,238,405 | 12/1980 | Felix | 548/166 |
| 4,388,314 | 6/1983 | Nannini et al. | 544/16 |
| 4,529,721 | 7/1985 | Nagata et al. | 514/191 |
| 5,039,702 | 8/1991 | Brandman et al. | 514/526 |

FOREIGN PATENT DOCUMENTS 0104432  8/1983  European Pat. Off. ............ 514/526
0156907  1/1981  Fed. Rep. of Germany ........ 558/14

OTHER PUBLICATIONS

CA 89(13):108129a 2,3-Dihalo ... homologs, Merianos et al. p. 796, 1978.
CA 112 (7):505882 Preparation ... microbicides, Austin et al., p. 268, 1990.

*Primary Examiner*—Mary C. Lee
*Assistant Examiner*—Joseph K. McKane

[57] ABSTRACT

3-Thiocyano-2-halo-2-propenenitriles are prepared which correspond to the formula:

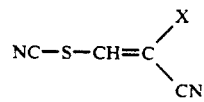

wherein X is a halogen.

These compounds have been found to exhibit a high degree of antimicrobial activity in industrial and commercial applications and compositions containing these compounds are so employed.

8 Claims, No Drawings

COMPOSITION AND USE OF 3-THIOCYANO-2-HALO-2-PROPENENITRILES AS ANTIMICROBIAL AGENTS

BACKGROUND OF THE INVENTION

The field of this invention is novel propenenitrile compounds which are useful as antimicrobial agents.

U.S. Pat. No. 5,039,702 discloses an α-halo-β-(substituted)thio-acrylonitrile of the formula:

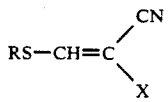

wherein X is a halogen and R is a lower alkyl, aryl, aralkyl, heterocyclo, or a thiocarbonyl group. This compound is taught to be useful as an effective antimicrobial agent.

The desirability of identifying or discovering new antimicrobial agents is widely recognized for several reasons. These include the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves some of these problems by disclosing a new compound which may be employed as an antimicrobial agent.

SUMMARY OF THE INVENTION

The present invention is a compound corresponding to the formula:

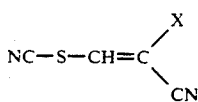

wherein X represents a halogen.

The present invention is also an antimicrobial composition comprising an inert diluent and an antimicrobially effective amount of a compound corresponding to the formula:

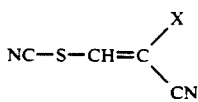

wherein X represents a halogen.

The present invention is also a method for inhibiting microorganisms in a microbial habitat comprising contacting said microbial habitat with an antimicrobially effective amount of a compound corresponding to the formula:

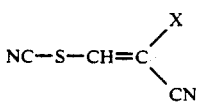

wherein X represents a halogen.

DETAILED DESCRIPTION OF THE INVENTION

The present invention is a 3-thiocyano-2-halo-2-propenenitrile compound corresponding to the formula:

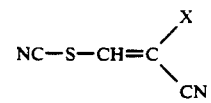

wherein X represents a halogen. Preferably, X represents chlorine or bromine.

The compounds of the present invention can be prepared by the reaction of an appropriately substituted 2,3-dihalo-2-propenenitrile precursor with an alkali metal thiocyanate, such as sodium thiocyanate or potassium thiocyanate. In carrying out this reaction, the appropriately substituted 2,3-dihalo-2-propenenitrile precursor and the alkali metal thiocyanate are typically mixed together in substantially equimolar amount. A preferred general reaction scheme is as follows:

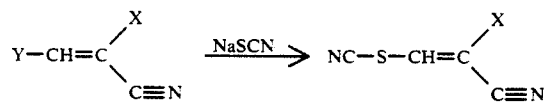

wherein X and Y independently represent a halogen.

As used herein, the term "appropriately substituted 2,3-dihalo-2-propenenitrile precursor" refers to a 2,3-dihalo-2-propenenitrile of the formula:

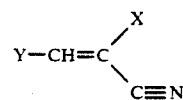

wherein X and Y independently represent a halogen, which is used as a precursor to produce a like-substituted 3-thiocyano-2-halo-2-propenenitrile. As used herein, the term "like-substituted 3-thiocyano-2-halo-2-propenenitrile" refers to a 3-thiocyano-2-halo-2-propenenitrile of the formula:

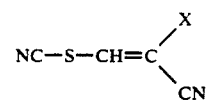

wherein X represents a halogen but wherein X is identical to the X of the appropriately substituted 2,3-dihalo-2-propenenitrile used as a precursor to produce the like-substituted 3-thiocyano-2-halo-2-propenenitrile. Thus, for example, 2,3-dichloro-2-propenenitrile is an appropriately substituted 2,3-dihalo-2-propenenitrile which is used as a precursor to produce 3-thiocyano-2-chloro-2-propenenitrile, the like-substituted 3-thiocyano-2-halo-2-propenenitrile.

A preferred method of preparing the compounds of the present invention is to carry out the reaction of the appropriately substituted 2,3-dihalo-2-propenenitrile precursor at room temperature in the presence of an inert, water-miscible solvent such as acetonitrile, tetrahydrofuran, dioxane, dimethylsulfoxide, isopropanol, polyglycols and their ethers, or dimethylformamide. Preferably, the reactions are carried out at 0° C. under an ambient pressure of inert gas. Subsequent to the addition of the appropriate reaction materials, the reaction mixture is preferably allowed to stir at a temperature of between about 25° C. to about 60° C. for a period of between about 2 to about 24 hours in order to increase the reaction rate and promote extinction of the limiting reagent. Final work-up of the reaction mixture then provides the desired final product.

The reaction rate of this preferred method of preparing the compounds of the present invention is conveniently controlled by the rate of alkali metal thiocyanate addition coupled with external cooling. Room temperature, however, may be used as the starting reaction temperature to increase the reaction rate. The reaction rate may also be controlled by the amount of inert, water-miscible solvent used. An increase in the amount of inert, water-miscible solvent will typically make the reaction mixture more homogeneous.

Advantages of using this preferred method of preparing the compounds of the present invention include mild reaction conditions, a high yield reaction, relatively inexpensive reagents, and a short reaction time. In addition, by using an inert, water-miscible solvent, a solvent extraction step can be eliminated because a desired product may be directly formulated as compared to a reaction process that uses a water-immiscible solvent to isolate the desired product. The reaction yield of this preferred method is also sufficiently high such that purification of a desired final product may not be required.

Tetraethylene glycol, for example, is a common formulating solvent for paints, pigment slurries, latexes, and metal working fluids. By using tetraethylene glycol as the inert, water-miscible solvent in the reaction, a desired composition may be directly formulated which could be directly used into a paint, pigment slurry, latex, or metal working fluid product.

Synthesis of Starting Materials

The synthesis of the appropriately substituted 2,3-dihalo-2-propenenitrile precursor begins with the halogenation of acrylonitrile to form 2,2,3-trihalopropionitrile. This halogenation is straightforward and is described in the art, such as in N. C. Larette, "The Addition of Chlorine to Acrylonitrile", *J. Org. Chem.*, Vol. 26, pp. 2324-2327 (1960). Overall yields of over 90 percent based on acrylonitrile are achievable.

Dehydrohalogenation of 2,2,3-trihalopropionitrile yields an isomeric mixture of 2,3-dihaloacrylonitrile. This dehydrohalogenation can be carried out by heating the 2,2,3-trihaloacrylonitrile in the presence of a catalyst with yields of 80 to 100 percent. Purification of the 2,3-dihaloacrylonitrile prior to subsequent reaction is optional. This dehydrochlorination is straightforward and is described in the art, such as in U.S. Pat. No. 2,385,550 or U.S. Pat. No. 3,527,787.

The synthesis of an alkali metal thiocyanate is straightforward and is described in the art, such as in Gluud, Keller, and Schultze, *Ber. Ges Kohlentech*, I, 1774 (1932); Hughes and Mead, *J. Chem. Soc.*, 2282 (1929); or King and Parlington, *Trans. Faraday Soc.*, 23, 522 (1927).

The following examples illustrate the present invention and the manner by which it can be practiced but, as such, should not be construed as limitations upon the overall scope of the same.

EXAMPLE 1

Preparation of 3-Thiocyano-2-Chloro-2-Propenenitrile

A solution of 2,3-dichloro-2-propenenitrile (5 g, 0.040 mole) in 75 ml of acetonitrile is treated with sodium thiocyanate (13.26 g, 0.163 mole) in one lot at room temperature. After 10 minutes the reaction solution becomes light brown in color. The progress of the reaction is monitored by gas chromatography. The resultant reaction mixture is stirred for 12 hours at room temperature. The solids are filtered and the filtrate is concentrated to half of its volume and then extracted twice with 100 ml portions of dichloromethane. The combined dichloromethane extracts are dried over anhydrous sodium sulfate, filtered and concentrated on a rotary evaporator to yield 3.0 g of crude product. A calculated overall yield of 40 percent is achieved.

The crude reaction product is purified by recrystallization from hexane yielding 2.8 g of colorless needles of 3-thiocyano-2-chloro-2-propenenitrile in greater than 99.5 percent purity. The structure identity is confirmed by proton and carbon nuclear magnetic resonance spectroscopy, infrared spectroscopy and gas chromatography/mass spectrometry.

Antimicrobial Activity

The compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, not all of the compounds disclosed herein are active at the same concentrations or against the same microbial species. That is, there is some compound-to-compound variation in antimicrobial potency and spectrum of antimicrobial activity.

The present invention is also directed to a process of using such 3-thiocyano-2-halo-2-propenenitriles as an antimicrobial agent. This process is a method for inhibiting microorganisms which comprises contacting said microorganisms or habitat thereof with an effective amount of the compounds of this invention.

The antimicrobial compounds of this invention may be added directly to aqueous formulations susceptible to microbial growth, either undiluted or dissolved in organic solvents such as glycols, alcohols, or acetone. They may also be added alone or in combination with other preservatives.

As used herein, the term "microorganism" is meant to refer to bacteria, fungi, viruses, algae, subviral agents and protozoa.

As used herein, the term "antimicrobially effective amount" refers to that amount of one or a mixture of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular compound tested and microorganism treated. Also, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grow. Typically, such a microbial habitat will be an area that comprises a moisture, nutrient, and/or an oxygen source such as, for example a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

The minimum inhibitory concentration (MIC) for the compounds is determined for 9 bacteria, using nutrient agar, and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5. Malt yeast agar is prepared by adding 3 g yeast extract and 45 g malt agar per liter of dionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentation of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are place din individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respective American Type Culture Collection (ATCC) identification numbers.

TABLE I

| Organisms used in the Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables II and III, the MIC values of the compounds as compared to the MIC of a standard commercial preservative (DOWICIL ™ 75, a trademark of The Dow Chemical Company, with 1-(3-chloroallyl)-3,5,7-triaza-1-azoniaadamantane chloride as the active agent) are set forth for the bacteria organisms and yeast/fungi organisms which are listed in Table I.

TABLE II

| Minimum Inhibitory Concentrations for Test Compounds in Bacteria Species (in ppm) | | | | | | | | | |
|---|---|---|---|---|---|---|---|---|---|
| | ORGANISMS | | | | | | | | |
| Compound | Bs | Ea | Ec | Kp | Pv | PRD | Pa | Sc | Sa |
| DOWICIL ™ 75 | | | | | | | | | |

TABLE II-continued

| | Minimum Inhibitory Concentrations for Test Compounds in Bacteria Species (in ppm) | | | | | | | | |
|---|---|---|---|---|---|---|---|---|---|
| | ORGANISMS | | | | | | | | |
| Compound | Bs | Ea | Ec | Kp | Pv | PRD | Pa | Sc | Sa |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| 3-Thiocyano-2-chloro-2-propenenitrile | | | | | | | | | |
| pH 6.8 | 25 | 250 | 100 | 100 | 50 | 250 | 250 | 100 | 50 |
| pH 8.2 | 500 | >500 | >500 | 500 | >500 | >500 | 500 | >500 | 500 |

TABLE III

| | Minimum Inhibitory Concentrations for Test Compounds in Yeast/Fungi Species (in ppm) | | | | | | |
|---|---|---|---|---|---|---|---|
| | ORGANISMS | | | | | | |
| COMPOUND | An | Ca | Pc | Sc | Tv | Ap | Fo |
| DOWICIL TM 75 | >500 | >500 | >500 | 500 | >500 | >500 | >500 |
| 3-Thiocyano-2-chloro-2-propenenitrile | 2.5 | 2.5 | 2.5 | 2.5 | 5 | 2.5 | 2.5 |

What is claimed is:

1. A compound corresponding to the formula:

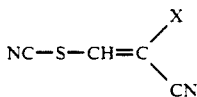

wherein X represents a halogen.

2. The compound of claim 1 wherein X represents chlorine.

3. An antimicrobial composition comprising an inert diluent and an antimicrobially effective amount of a compound corresponding to the formula:

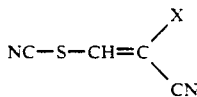

wherein X represents a halogen.

4. The composition of claim 3 wherein X represents chlorine.

5. The composition of claim 3 wherein the compounds is present in the composition in an amount to provide from about 1 part per million to about 5,000 parts per million by weight of the compound to an antimicrobial habitat that is contacted with the composition.

6. A method for inhibiting microorganisms in a microbial habitat comprising contacting said microbial habitat with an antimicrobially effective amount of a compound corresponding to the formula:

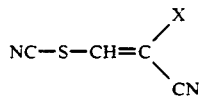

wherein X is a halogen.

7. The method of claim 6 wherein the compound is used in an amount to provide from about 1 part per million to about 5,000 parts per million by weight of the compound to the microbial habitat.

8. The method of claim 6 wherein X represents chlorine.

* * * * *

UNITED STATES PATENT AND TRADEMARK OFFICE
CERTIFICATE OF CORRECTION

PATENT NO. : 5,157,051
DATED : October 20, 1992
INVENTOR(S) : Kalakota S. Reddy et al.

It is certified that error appears in the above-indentified patent and that said Letters Patent is hereby corrected as shown below:

Title page, item [75], Inventors, "Kalakota S. Reddy; Thomas L. Siddall; Connie L. DeFord, all of Midland, Mich." should correctly read as -- Kalakota S. Reddy; Thomas L. Siddall, both of Midland, Mich.--

Signed and Sealed this

Twelfth Day of October, 1993

Attest:

BRUCE LEHMAN

*Attesting Officer*    *Commissioner of Patents and Trademarks*